(12) United States Patent
Jun et al.

(10) Patent No.: US 6,299,902 B1
(45) Date of Patent: Oct. 9, 2001

(54) ENHANCED TRANSDERMAL ANESTHESIA OF LOCAL ANESTHETIC AGENTS

(75) Inventors: H. Won Jun; Lisheng Kang, both of Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/356,137

(22) Filed: Jul. 19, 1999

Related U.S. Application Data

(60) Provisional application No. 60/134,888, filed on May 19, 1999.

(51) Int. Cl.[7] ...................................................... A61K 9/70
(52) U.S. Cl. .......................... 424/449; 424/447; 424/443; 424/78.05; 424/78.07; 514/817; 514/887; 514/947; 514/969
(58) Field of Search ..................................... 424/449, 447, 424/443, 78.05, 78.07; 514/817, 887, 947, 969

(56) References Cited

U.S. PATENT DOCUMENTS

| 4,529,601 | 7/1985 | Broberg et al. . |
| 4,562,060 | 12/1985 | Broberg et al. . |
| 4,990,340 | 2/1991 | Hidaka et al. . |
| 5,069,908 | 12/1991 | Henley . |
| 5,120,544 | 6/1992 | Henley . |
| 5,885,597 | 3/1999 | Botknecht et al. ................... 424/401 |
| 5,922,340 | 7/1999 | Berde et al. . |

FOREIGN PATENT DOCUMENTS

| 1093897 A | 4/1993 | (CN) . |
| 1565775 A | 4/1980 | (GB) . |
| 64 834 A | 3/1994 | (HU) . |
| 60053150 A | 3/1985 | (JP) . |
| 3090023 A | 4/1991 | (JP) . |
| 03291221 A | 12/1991 | (JP) . |
| 6-199701 | 7/1994 | (JP) . |
| 7291856 A | 11/1995 | (JP) . |
| 9208464 A | 8/1997 | (JP) . |
| 09-255565 A | 9/1997 | (JP) . |
| WO 91/04733 | 4/1991 | (WO) . |
| WO 91/12010 A | 8/1991 | (WO) . |
| WO 92/13540 A | 8/1992 | (WO) . |
| WO 94/05273 A | 3/1994 | (WO) . |
| WO 94/05271 A | 8/1994 | (WO) . |
| WO 96/11693 A1 | 4/1996 | (WO) . |
| WO 98/51283 | 11/1998 | (WO) . |

OTHER PUBLICATIONS

Agoston et al., Topical drug for treatment of gingival diseases, *Chemical Abstracts,* 117(26):258212 (1992). Abstract only (HU 60 126 A).

(List continued on next page.)

*Primary Examiner*—Michael A. Williamson
(74) *Attorney, Agent, or Firm*—Mueting, Raasch & Gebhardt, P.A.

(57) ABSTRACT

A novel topical anesthetic preparation is characterized by improved transdermal absorption and efficacy. In a preferred embodiment, the topical preparation contains at least one local anesthetic agent and at least two melting point depressing agents. Also provided is a two-phase liquid composition that contains aqueous and oil phases, the oil phase having a relatively high concentration of a local anesthetic agent to enhance transdermal absorption and efficacy when incorporated into a topical anesthetic preparation. A preferred topical anesthetic preparation includes lidocaine or tetracaine, thymol or menthol, and ethyl alcohol or isopropyl alcohol. The preparation is expected to be safe and effective in obtaining transdermal anesthesia on intact skin and mucous membrane of adults, children, infants and newborns.

69 Claims, 2 Drawing Sheets

A

B

OTHER PUBLICATIONS

Kang et al., "Physicochemical studies of lidocaine–menthol binary systems for enhanced membrane transport", *Int. J. Pharm,* 206:35–42 (2000).

Nortier et al., "Preparation and stability testing of hydrogel for topical analgesia", *Pharmacy World and Science,* 17(6):214–217 (1995).

Nyqvist–Mayer et al., "Phase Distribution Studies on an Oil–Water Emulsion Based on Eutecic Mixture of Lidocaine and Prilocaine as the Dispersed Phase", *Journal of Pharmaceutical Sciences,* 74(11):1192–1195 (1985).

Nyqvist–Mayer et al., "Drug Release Studies on an Oil–Water Emulsion Based on a Eutectic Mixture of Lidocaine and Prilocaine as the Dispersed Phase", *Journal of Pharmaceutical Sciences,* 75(4):365–373 (1986).

American Academy of Pediatrics, *Circumcision Policy Statement (RE9850),* 103(3): 686–693, Mar. (1999).

Buckley et al., "Eutectic Lidocaine/Prilocaine Cream. A Review of the Topical Anaesthetic/Analgesic Efficacy of a Eutectic Mixture of Local Anaesthetics (EMLA)," *Drugs,* 45(1): 126–151 (1983).

D'Amour et al., "A Method For Determining Loss Of Pain Sensation," *J. Pharmacol. Exp. Ther.,* 72: 74–78 (1941).

Evers et al., "Dermal Effects of Compositions Based on the Eutectic Mixture of Lignocaine and Prilocaine (EMLA). Studies in Voulunteers," *Br. J. Anaesth.,* 57:997–1005(1985).

Jakobson et al., "Methemoglobinemia Associated with a Prilocaine–Lidocaine Cream and Trimetoprim–Sulphamethoxazole. A Case Report," *Acta Anaesthaesialogica Scandinavica,* 29: 453–455 (1985).

Lichtman et al., "Investigation of Brain Sites Mediating Cannabinoid–Induced Antinociception in Rats: Evidence Supporting Periaqueductal Gray Involvement," *J. Pharmacol Exp. Ther.,* 276: 585–593 (1996).

McCafferty et al., "In Vivo Assessment of Percutaneous Local Anaesthetic Perparations," *Br. J. Anaesth.,* 62: 17–21 (1989).

Molodecka et al., "Comparison or percutaneous anaesthesia for venous cannulation after topical application of either amethocaine of EMLA cream," *Br. J. Anaesth.,* 72: 174–176 (1994).

Pesenti et al., "Effect on the growth of 5 bacterial species of oral flora of a menthol–thymol–salicyclic acid–tetracaine chlorhydrate compound", *Rev Odontostomatol* (Paris) France, 16(6): 371–373, Nov/Dec (1987). (Abstract Included).

Physician's Desk Reference, 49th Ed., Medical Economics Data Production Company, Montvale, NH (1995).

Russell et al., "A Risk–Benefit Assessment of Topical Percutaneous Local Anaesthetics in Children," *Drug Safety,* 16(4): 279–287 (1997).

Taniguchi et al., "Antinociceptive effects of counterirritants," *Folia Pharmacologica Japonica* (Japan), 104/6: 433–466 (1994) (Abstract Included).

Tseng et al., "Pretreatment with Pertussis Toxin Differentially Modulates Morphine– and β–Endorphin–induced Antinociception in the Mouse,"*J. Pharmacol. Exp. Ther.,* 279: 39–46 (1997).

Vaz et al., "Antinociceptive Action of 2–(4–Bromobenzoyl)–3–Methyl–4, 6–Dimethoxy Benzofuran, a Novel Xanthoxyline Derivative on Chemical and Thermal Models of Nociception in Mice," *J. Pharmacol. Exp. Ther.,* 278: 304–312 (1996).

Woolfson et al., "Concentration–Response Analysis of Percutaneous Local Anaesthetic Formulations," *Br. J. Anaesth.,* 61: 589–592 (1988).

ENHANCED TRANSDERMAL ANESTHESIA OF LOCAL ANESTHETIC AGENTS

This patent application claims the benefit of U.S. provisional patent application No. 60/134,888, filed May 19, 1999.

BACKGROUND OF THE INVENTION

The search continues for a safe and effective topical anesthetic preparation that can ease the pain during dermal procedures, such as venipuncture, intravenous cannulation, punch biopsy and other small incisions, vaccination, and circumcision. A preparation that is safe for use in newborns is especially needed, since circumcision remains a common medical procedure performed on newborns, and existing scientific evidence demonstrates potential medical benefits of newborn male circumcision. Unfortunately, circumcision of infants is typically performed without any pain-relief treatment even though the American Academy of Pediatrics recommends procedural analgesia (AAP Circumcision Policy Statement, March 1999, pp. 686–693) because safe and effective topical preparations are not currently available.

EMLA cream (Astra Pharmaceuticals, Inc., Westboro, Mass.), a eutectic mixture of lidocaine 2.5% and prilocaine 2.5% in an emulsified topical cream (U.S. Pat. No. 4,562,060; U.S. Pat. No. 4,529,601), is the only topical anesthetic product currently marketed in many countries, including the United States, for use on intact skin. Because EMLA cream contains a relatively high concentration of local anesthetic in its oil phase, it exhibits improved efficacy on intact skin compared with other conventional local anesthetic formulations, which are effective only on mucous membranes.

Metabolites of prilocaine, however, are known to be responsible for methemoglobinemia, a serious condition characterized by the ferric form of hemoglobin with impaired oxygen-carrying capacity (B. Jakobson et al., *Acta Anaesthesialogica Scandinavica* 29: 453–455 (1985)). As a result, the use of EMLA in young children has been severely restricted. For example, in the United States, EMLA is currently contraindicated in infants under 3 months old (M. Buckley et al., Drugs 46:126–151 (1993)), and in infants up to 1 year of age who are also receiving methemoglobin-inducing agents (Physician's Desk Reference, 49$^{th}$ Ed., Medical Economics Data Production Company, Montvale, N.H. (1995)). In the United Kingdom, EMLA is not approved for use in children under 1 year of age (S. Russell et al., *Drug Safety* 16:279–287 (1997)). Also, the Drug Information Handbook, 4$^{th}$ Ed. (1996–1997), published by the American Pharmaceutical Association, states that EMLA cream should not be used in infants under the age of 1 month. Very young patients, and patients with glucose-6-phosphate deficiencies, show increased susceptibility to methemoglobinemia.

Lidocaine, on the other hand, is safe and is the most widely used local anesthetic agent. However, due to low permeability of lidocaine through the stratum corneum, the efficacy of lidocaine alone for topical anesthesia through intact skin has to date been extremely disappointing. Conventional lidocaine creams may be readily prepared by simply dissolving lidocaine in a suitable pharmaceutical oil and emulsified, but these creams can not effectively deliver lidocaine for transdermal anesthesia on intact skin. Efficacy can only be achieved when the concentration of lidocaine in the topical formulation is unacceptably high (e.g., greater than about 30% by weight), posing a risk of systemic toxicity. Limited by the intrinsic solubility of lidocaine in pharmaceutical oils, lidocaine concentration in the oil phase of conventional creams cannot reach the concentration that is necessary for effective transdermal delivery.

EMLA cream achieves higher concentrations of lidocaine in the oil phase compared to other creams by including prilocaine in the formulation, thereby facilitating the solid to oil phase transition of lidocaine. The resulting eutectic mixture has a lidocaine:prilocaine ratio that ranges from 20:80 to 58:42 (U.S. Pat. No. 4,562,060) and the commercially available product (EMLA) has a lidocaine:prilocaine ratio of 50:50. However, as noted above, prilocaine is known for causing methemoglobinemia in children.

A preparation containing lidocaine but little or no prilocaine would, therefore, have a significant clinical advantage over EMLA and would also expand the use of topical anesthetics in children and particularly in infants and newborns.

SUMMARY OF THE INVENTION

A novel composition is provided that can be readily formulated into a topical anesthetic preparation. Preferred embodiments of the anesthetic preparation of the invention are characterized by enhanced transdermal absorption and safe and effective transdermal anesthesia through intact skin. The composition has two liquid phases: an aqueous phase and an oil phase, wherein the oil phase has a relatively high concentration a local anesthetic agent, preferably lidocaine. An aqueous phase is a phase that comprises water. Preferably, both the aqueous phase and the oil phase are homogeneous. A "homogenous" aqueous phase or oil phase is a liquid phase in which none of the components is present in a solid state. The aqueous and oil phases of the composition of the invention are preferably homogenous phases at about 37° C.; more preferably, they are homogenous phases at about 25° C. It should nonetheless be understood that the invention also encompasses two phase liquid compositions that contain nonhomogenous aqueous and/or oil phases; that is, the presence of some solids in the aqueous phase or the oil phase, or both, is not necessarily excluded.

The concentration of the local anesthetic agent in the oil phase of the composition is preferably at least about 60%, by weight, of the weight of the oil phase; more preferably it is at least about 70% by weight, of the weight of the oil phase; even more preferably it is at least about 80%, by weight, of the weight of the oil phase; most preferably it is at least about 85%, by weight, of the weight of the oil phase of the composition.

A preferred two phase liquid composition of the invention contains:
  (a) a local anesthetic agent, preferably at least about 1% of the total composition, by weight, more preferably at least about 3% of the total composition, by weight, and preferably less than about 20% of the total composition, by weight, more preferably less than about 10% of the total composition, by weight;
  (b) a first melting point depressing agent, preferably in an amount of at least about 1/20 of the weight of the local anesthetic agent, more preferably at least about 1/10 of the weight of the local anesthetic agent; and preferably less than about 2/3 of the weight of the local anesthetic agent, more preferably less than about 1/4 of the weight of the local anesthetic agent;
  (c) a second melting point depressing agent, preferably at least about 1% of the total composition, by weight, more preferably at least about 5% of the total composition, by weight, most preferably at least about 10% of the total composition, by weight, and preferably less than about 30% of the total composition, by weight, more preferably less than about 20% of the total composition, by weight, most preferably less than about 15% of the total composition, by weight; and (d) water to 100%.

The local anesthetic agent is typically a solid at ambient temperature. However, it is to be understood that the term "solid" is used broadly to include hygroscopic compounds and other solids that, under certain conditions, take a semi-solid form. When the local anesthetic agent is a solid, melting of the solid yields an oil. The first melting point depressing agent is typically a solid or an oil at ambient temperature. When the first melting point depressing agent is a solid, melting of the solid yields an oil. Preferably, the local anesthetic agent and the first melting point depressing agent have melting points lower than about 200° C.; more preferably, they have melting points lower than about 160° C.; most preferably, they have melting points lower than about 120° C.

Methods for making the two phase liquid composition of the invention are also provided. Components of the composition are mixed together in amounts effective to form a two phase liquid composition consisting of an aqueous phase and an oil phase. Preferably, the aqueous and oil phases are homogeneous below about 37° C., more preferably they are homogenous at or below about 25° C. During mixing, at least a portion of the solid component(s) undergoes a solid to liquid phase transition; that is, it melts. If the solid component is semisolid or hygroscropic, at least a portion of the component(s) becomes oily during mixing. Simple mixing of the components at ambient temperature causes at least some melting of the solid components without heating. In some embodiments of the invention, an external source of heat is applied to the mixture to more quickly achieve a "melt." When an external source of heat is used during the preparation of the composition, the mixture is preferably maintained at a temperature of less than about 50° C.

The components of the two phase liquid composition of the invention partition between the aqueous phase and oil phase according to their individual physical and chemical properties to form an equilibrated system. For example, the local anesthetic agent can partition between the oil phase and the aqueous phase, in accordance with its relative solubility in each liquid phase.

Although the inventors do not intend to be bound by any particular theory or mechanism, it is believed that inclusion of the first and second melting point depressing agents in the mixture in accordance with the invention causes the solid component(s) to melt into the oil phase by depressing the melting point(s) of the solid component(s). More particularly, it is believed that inclusion of the first and second melting point depressing agents yields an oil phase having a higher concentration of the local anesthetic agent, such as lidocaine, than has previously been achieved. Increasing the concentration of the local anesthetic agent in the oil phase at ambient temperature is desirable because it enhances transdermal absorption and efficacy. In compositions of the invention, the concentration of the local anesthetic agent in the oil phase can reach about 87% or higher, by weight, of the weight of the oil phase. The remaining oil phase typically contains amounts of the melting point depressing agents and a trace amount of water.

The term "two phase melt system" is used herein, particularly in the Examples, to describe a two phase liquid composition of the invention that has been generated by combining the components of the composition to effect an oily "melt state" below about 37° C., preferably at or below about 25° C. It should be nonetheless understood that the composition of the invention is by no means limited to any particular method of making the composition. If no solids (e.g., crystals) remain in the oil phase and the aqueous phase of a resulting composition, it is considered that a complete melt has occurred; if solids remain in either the oil phase or the aqueous phase, only a partial melt has achieved. Compositions resulting from both complete or partial melts are included in the invention, although compositions resulting from complete melts are preferred.

The two phase liquid compositions of the invention are readily formulated into a cream, an emulsion, an ointment, a lotion, a lipophilic organogel, a patch, or the like, that is effective in obtaining transdermal anesthesia on intact skin, and these pharmaceutical formulations are encompassed by the invention. Notably, a cream prepared from a two phase liquid composition of the invention is shown herein to be at least as effective as EMLA in in vivo efficacy studies in mice and humans. A typical cream contains, by weight, at least about 0.5% local anesthetic agent, more preferably, at least about 1% local anesthetic agent, most preferably at least about 3% local anesthetic agent; and less than about 20% local anesthetic agent, more preferably, less than about 10% local anesthetic agent. A preferred cream contains lidocaine or tetracaine as the local anesthetic, and thymol as the first melting point depressing agent.

The pharmaceutical formulation of the invention can also take the form of a transdermal patch, plaster, or occlusive dressing. In addition, the oil phase of the two phase liquid composition of the invention can be combined with a pharmaceutically acceptable miscible solvent, and the resulting liquid mixture constitutes an anesthetic preparation that can be applied directly to the skin or mucous membrane. For example, the anesthetic liquid preparation can be dabbed or applied to the dental gum of a patient during dental work or to relieve toothache or teething pain.

The invention further provides a method for anesthetizing intact skin that employs topical application of a pharmaceutical preparation of the invention. The pharmaceutical preparation is expected to be safe and effective in obtaining transdermal anesthesia on intact skin of adults, children, infants and newborns, and is suitable for use in veterinary or agricultural husbandry applications as well.

The invention further provides a method for obtaining transdermal anesthesia in animal, preferably a mammal, more preferably a human, comprising administering an anesthetic preparation of the invention to intact skin or mucous membrane of the animal. The preparation can be administered to the intact skin of the animal, or wounded skin. Optionally, the method includes covering the preparation with a dressing, such as a gauze, bandage, patch and the like. Alternatively, the preparation can be administered using a transdermal patch. The method can be performed whenever transdermal anesthesia is required or desired, such as prior to surgical incision, dental work, vaccination, needle insertion, and the like.

The concept of the two phase melt system can be extended to facilitate the preparation of other potential "melt" therapeutic compositions. The invention thus further includes a method for preparing an oil containing a therapeutic agent that involves adding at least one melting point depressing agent, preferably an alcohol, and water to a therapeutic agent to form a two phase liquid composition consisting of an aqueous phase and an oil phase, wherein the oil phase has a relatively high concentration the therapeutic agent. The therapeutic agent is typically a solid at ambient temperature. The aqueous and oil phases of the composition of this aspect of the invention are preferably homogenous phases at about 37° C.; more preferably, they are homogenous phases at about 25° C. It should nonetheless be understood that this aspect of the invention also encompasses two phase liquid compositions that contain nonhomogenous aqueous and/or oil phases; that is, the presence of some solids in the aqueous phase or the oil phase, or both, is not necessarily excluded. Preferably, the oil phase of the two phase liquid composition of this aspect of the invention has a concentration of the therapeutic agent that is, by weight, at least about 50% of the weight of the oil phase. More preferably, the concentration of the therapeutic agent in the oil phase is at least about 60%, by weight, of the weight of the oil phase; still more preferably, it is at least about 70%, by weight, of the weight of the oil phase; most preferably, it is at least about 80%, by weight, of the weight of the oil phase. The therapeutic agent is one that forms an oil upon melting, and preferably has a melting point of less than about 200° C., more preferably less than about 160° C., most preferably less than about 120° C. It is believed that the oil phase is formed because the aqueous alcohol depresses the melting point of the therapeutic agent although the inventors do not intend the invention to be limited by any particular theory or mechanism. Optionally, one or more additional melting point depressing agents, as described herein, can be added to the mixture to further depress the melting point of the therapeutic agent. The addition of the alcohol and optional additional melting point depressing agents causes partial or complete melting of the solid, at least a portion of which remains in the resulting oil phase which has a higher concentration of the therapeutic agent in the oil phase than previously attainable. The method of preparing the therapeutic composition can be performed at about 20° C. to about 25° C. (i.e., ambient temperature), but the heating of the mixture to facilitate the melting when needed or desired is also envisioned. The alcohol is preferably ethyl alcohol, isopropyl alcohol, propylene glycol, polyethylene glycol, or a combination thereof; more preferably, it is isopropyl alcohol or ethyl alcohol.

DETAILED DESCRIPTION

Figure 1:
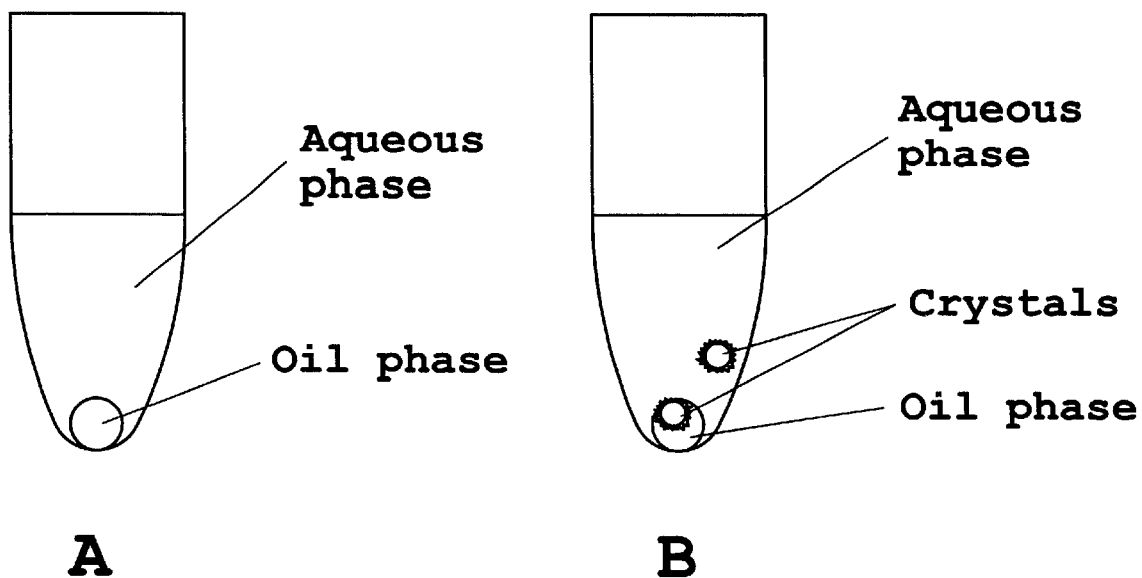
FIG. 1 illustrates (A) a two phase liquid composition having a homogenous aqueous phase and a homogenous oil phase and (B) a two phase liquid composition wherein crystals are present in the aqueous phase and the oil phase, rendering the aqueous and oil phases nonhomogenous.

The local anesthetic is preferably provided in its base form, and is preferably lidocaine (also known as lignocaine), tetracaine, benzocaine, prilocaine, procaine, mepivacaine, bupivacaine or etidocaine. Lidocaine is 2-diethylamino-N-[2,6-dimethylphenyl]acetamide and is available under the tradename XYLOCAINE. Tetracaine is 2-dimethylaminoethyl-4-n-butylaminobenzoate and is available under the tradename PONTOCAINE. Prilocaine is 2-propylamino-N-(2-tolyl)propionamide and is available under the tradename CITANEST. Procaine is 2-diethylaminoethyl p-aminobenzoate and is available under the tradename of AMINOCAINE. Mepivacaine is 1-methyl-2-(2,6-xylylcarbomoyl)piperidine and is available under the tradename CARBOCAINE. Benzocaine is 4-aminobenzoic acid ethyl ester and is available under the tradename AMERICAINE. Bupivacaine is 1-butyl-2-(2,6-cycylcarbomoyl)piperidine and is available under the tradename MARCAINE. Etidocaine is 2-ethylpropylamino-2,6-n-butyroxylidide and is available under the tradename DURANEST. In embodiments of the composition containing both lidocaine and prilocaine, the lidocaine:prilocaine ratio is preferably higher than about 60:40.

The first melting point depressing agent can be thymol, menthol, methyl salicylate, phenyl salicylate, butylated hydroxytoluene, butylated hydroxyanisole, S(+)-ibuprofen, R(−)-ibuprofen, cineole, eugenol, capsaicin, eucalyptol, any local anesthetic agent not already included as the local anesthetic, or any combination thereof. The second melting point depressing agent is an alcohol, preferably ethyl alcohol, isopropyl alcohol, propylene glycol, polyethylene glycol, or any combination thereof.

The two phase liquid composition of the invention can be made by intimately mixing a local anesthetic agent (LA), one or more first melting point depressing agents (MP-A), one or more second melting point depressing agents (MP-B), and water within the weight ranges shown in Table 1.

TABLE 1

| | |
|---|---|
| LA | 1–20%ᵃ |
| MP-A | ¹⁄₂₀ to ²⁄₃ wt of LA |
| MP-B | 1–30%ᵃ |
| Water q.s. | 100%ᵃ |

ᵃamounts are percentages of the total composition by weight

The local anesthetic, LA, is preferably lidocaine, tetracaine, prilocaine, procaine, etidocaine, mepivacaine, benzocaine or bupivacaine. More preferably, LA is lidocaine or tetracaine. The first melting point depressing agent, MP-A, can be any or any combination of thymol, menthol, methyl salicylate, phenyl salicylate, butylated hydroxytoluene, butylated hydroxyanisole, S(+)-ibuprofen, R(−)-ibuprofen, cineole, eugenol, capsaicin, eucalyptol, or any local anesthetic compound not used as LA. Preferably, MP-A is thymol, menthol, or S(+)-ibuprofen, more preferably it is thymol. The second melting point depressing agent, MP-B, is an alcohol, and is preferably any or any combination of ethyl alcohol, isopropyl alcohol, propylene glycol or polyethylene glycol. The water component of the composition can be pure water or an aqueous solution. An aqueous solution can be a buffer and/or can contain a solute, such as a salt. Preferably the aqueous solution has a pH of about 8 to about 10. The water used to make the composition is preferably distilled and filtered; more preferably, it is distilled, filtered and deionized.

The order in which the components are mixed is not important; they can be mixed in any order. For example, it is often convenient to first mix the solids (e.g., the local anesthetic and the first melting point depressing agent) then add a liquid mixture of alcohol (the second melting point depressing agent) and water.

Thymol (5-methyl-2-isopropyl-1-phenol) is widely used in many pharmaceutical and mouthwash products with proven safety. Interestingly, when lidocaine crystals are mixed directly with thymol crystals, some melting point depression of both lidocaine and thymol occurs and an oil typically forms. However, it is only possible to obtain a homogeneous oil at ambient temperature (that is, at about 20° C. to about 25° C.) with the lidocaine:thymol ratio between about 7:3 and 3:7 by weight (see Example I, section A). At higher lidocaine:thymol ratios, lidocaine crystals remain in the oil phase; that is, the oil phase is not homogenous. The two-phase melt system of the invention, which utilizes a second melting point depressing agent, such as ethyl alcohol or isopropyl alcohol, and water, was discovered to achieve a higher concentration of the LA in the oil phase than has previously been attainable.

It was discovered that ethyl alcohol in water, without a first melting point depressing agent, also depresses the melting point of lidocaine, but when it is used without a first melting point depressing agent, a homogenous oil phase is obtained only when the ethyl alcohol content in the composition is 25% by weight or higher (see Example I, section B), which is not practical for preparation of a cream and may lead to instability of a cream or other drug delivery system prepared.

The two-phase liquid composition of the invention can be directly formulated into a cream or other desired topical anesthetic preparation using methods well-known to those of skill in the art. To form a preparation suitable for topical application to a patient, the two phase liquid composition is introduced into a pharmaceutically acceptable carrier, and is, for example, emulsified with a small amount of one or more surfactants. Optionally, the pharmaceutical formulations include one or more accessory ingredients including excipients, buffers, surface active agents, thickeners, preservatives, permeation enhancers, fragrance, coloring agents, and the like. Also optionally, the pharmaceutical formulations of the invention include antimicrobial agents, antiseptics, antioxidants, permeation enhancers, vitamins, and the like. Antioxidants include ascorbic acid and α-tocopherol.

The high concentration of the local anesthetic agent in the oil phase of the composition of the invention improves transdermal absorption and anesthetic efficacy of the active components through intact skin. Local anesthesia is obtained by topical application of the anesthetic preparation at the intended skin surface. Preferably, the anesthetic preparation is applied at a dose of about 0.1 g to about 1 g of the anesthetic preparation per $cm^2$ of skin. The amount of local anesthetic agent administered per dose is preferably about 1.0 mg to about 100 mg/$cm^2$ of skin; more preferably it is about 3.0 to about 50 mg/$cm^2$ of skin.

Although preferred for use on intact skin, the composition can also be formulated for use on wounded skin or on mucous membranes such as dental gums. Examples of procedures that can be performed on skin or mucous membranes that can be anesthesized according to the invention include circumcision, needle insertion, incision, punch biopsy, nevi excision, dental work, toothache, and relief of teething pain in infants and the like.

The invention is illustrated by the following examples. However, the particular materials and amounts thereof recited in these examples, as well as other conditions and details, are to be interpreted to apply broadly in the art and should not be construed to unduly restrict or limit the invention in any way.

EXAMPLE 1

Melting Point Depression of Lidocaine by Thymol and Ethyl Alcohol

A. Melting Point Depression of Lidocaine (L) by Thymol (T)

The melting points of lidocaine and thymol are 68° C. and 52° C., respectively. After preparing and storing the mixtures consisting of lidocaine and thymol in the L:T ratios from 1:9 to 9:1 (w:w) at 25° C., the melting states of the mixtures were examined weekly for 3 months using an optical microscope. Although the mixtures within L:T ratios of 3:7 to 7:3 (w:w) spontaneously form a homogeneous oil at ambient temperature, some crystals and oil co-exist in the mixtures outside this range. For example, in the mixture with the L:T ratio of 8:2 (w:w), a large portion of lidocaine remains as crystalline solid at 25° C.

Lidocaine and thymol were chemically stable in the mixtures that formed a homogenous oil. Compositional analysis of the mixture containing 50% lidocaine and 50% thymol (w:w) that was stored at 25° C. for 6 months, utilizing gas chromatography-mass spectrometry (GC-MS), showed essentially complete recovery of both lidocaine (101.6±3.98%) and thyme (99.36±2.22%) (n=3).

B. Melting Point Depression of Lidocaine (L) by Ethyl Alcohol (E) in Aqueous Dispersions Lidocaine was dispersed into a solution containing ethyl alcohol and water, and oil droplets formed at 25° C., which is below the melting point of lidocaine. To measure the effect of ethyl alcohol on the melting point depression of lidocaine in the aqueous dispersion, lidocaine (0.5 g) was mixed (at 25° C.) with 1.0 g, 1.5 g, 2.0 g, and 2.5 g of ethyl alcohol, and then a pH 9.2 phosphate buffer was added up to 10 g. Replicate samples of these mixtures were prepared at room temperature then stored at 25° C., 15° C., and 4° C. During storage, the melt states of the samples were examined weekly for 3 months using an optical microscope. Table 2 shows that when the ethyl alcohol contents were 20% or less, lidocaine did not completely melt at 25° C. When the ethyl alcohol contents were 25% (or higher, not shown in the table), the lidocaine crystals undergo a solid to liquid phase change into an oil even at 15° C. Clearly, the melting point of lidocaine in these dispersions is inversely dependent on the ethyl alcohol content; that is, the higher the ethyl alcohol content, the lower the melting point of lidocaine.

After ultracentrifugation, a portion of the oil phase was removed from the mixture containing 25% ethyl alcohol using a 25 μL microsampling tube, and the weight was measured using a tared weighing. The oil was then dissolved in methylene chloride and analyzed by GC-MS. The results show that the concentration of lidocaine was 73% (w:w) in the oil, indicating that the oil was a mixture of lidocaine, ethyl alcohol, and possibly some water.

TABLE 2

Melt States of Dispersions Containing Lidocaine[a], Ethyl Alcohol (E), and Water at Different Temperatures

| °C\E %[b] | 10 | 15 | 20 | 25 |
|---|---|---|---|---|
| 25 | S | S | S | O |
| 15 | S | S | S | O |
| 4 | S | S | S | S |

[a]5% of total composition, by weight
[b]% of total composition, by weight
S - solid crystals present (see FIG. 1-B)
O - oil without crystals (see FIG. 1-A)

C. Melting Point Depression of Lidocaine (L) by Thymol (T) and Ethyl Alcohol (E) in Aqueous Dispersions Since thymol and ethyl alcohol can individually depress the melting point of lidocaine, the effect of the two compounds in combination on the melting point of lidocaine was studied.

A 3-factor factorial design as shown in Table 3 was used to examine the melting states of lidocaine in the presence of both thymol and ethyl alcohol simultaneously at different temperatures. Since thymol alone is capable of depressing the melting point of lidocaine at and below 25° C. within the L:T ratios of 3:7–7:3 (w:w), only the higher L:T ratios higher than this range were included in the study.

TABLE 3

Melt States of Dispersions Containing Lidocaine (L), Thymol (T), Ethyl Alcohol (E), and Water at Different Temperatures

| L:T[a] | °C. | 10% E[a] | 15% E | 20% E | 25% E |
|---|---|---|---|---|---|
| 90:10 | 25 | S | O[III] | O[IV] | O |
|  | 15 | S | S | S | O |
|  | 4 | S | S | S | O |
| 85:15 | 25 | O[I] | O[II] | O[V] | O |
|  | 15 | O | O | O | O |
|  | 4 | S | S | S | O |
| 80:20 | 25 | O | O | O | O |
|  | 15 | O | O | O | O |
|  | 4 | S | O | O | O |

S - solid crystal present (see FIG. 1B)
O - oil without crystals (see FIG. 1A)
[a]L:T and % E by weight Lidocaine (0.5 g) was mixed (at ambient temperature) with 0.125 g, 0.088 g, and 0.056 g of thymol and 1.0 g, 1.5 g, 2.0 g, and 2.5 g of ethyl alcohol, then a pH 9.2 phosphate buffer was added up to 10 g. Replicate samples of these mixtures were prepared at 25° C. and were stored at 25° C., 15° C., and 4° C. for three months. During storage, the melt states of the mixtures were examined weekly for three months using an optical microscope. The two types of dispersions typically observed are shown in FIG. 1. The results in Table 3 show that there is a clear relationship among the L:T ratios, ethyl alcohol content, and melt states of lidocaine in the mixture. The lower the L:T ratios and the higher the ethyl alcohol content, the lower the melting point range of the solid components in the mixture as shown by the attainment of the melt state. Comparing these results, as well as the effect of thymol alone on the melting point of lidocaine with the data in Table 2, it is clear that a more pronounced melting point depression effect was demonstrated when thymol and ethyl alcohol were used simultaneously rather than individually. Thus, the use of thymol and ethyl alcohol in combination allows the preparation of the two-phase melt systems with highest possible L:T ratio and lowest ethyl alcohol content at 25° C.

D. Distribution of Lidocaine (L) and Thymol (T) Between the Aqueous and Oil Phases in the Melt Systems As shown in Table 3, Melt Systems I, II, III, IV, and V consisted of the homogeneous oil and the aqueous phase without crystals present at 25° C. Compared with other melt systems listed in the table, these systems contained relatively lower concentrations of thymol and ethyl alcohol and accordingly were selected for further study, since minimizing the concentrations of thymol and ethyl alcohol in the compositions while still retaining high concentrations of lidocaine in the oil phase is preferred.

After separating the oil droplets from the aqueous phase by ultra-centrifugation at 20,000 rpm for 30 minutes at 25° C., the oil phases from Melt Systems II, III, IV, and V were analyzed by GC-MS, as described above, to determine both lidocaine and thymol concentrations. The aqueous phase from Melt System III was also analyzed after the extraction with methylene chloride. The chemical compositions of the oil phase in these melt systems are shown in Table 4.

TABLE 4

Composition of Oil Phase in Selected Two-Phase Melt Systems

| Melt Systems | % L[b] | % T[b] | % Residual[c] |
|---|---|---|---|
| II[a] | 80.1 | 15.1 | 4.8 |
| III[a] | 87.0 | 10.6 | 2.4 |
| IV[a] | 85.9 | 11.2 | 2.9 |
| V[a] | 81.2 | 16.2 | 2.6 |

[a]source: Table 3
[b]% L or T = amount (g) of lidocaine or thymol detected per 100 g of the oil phase
[c]Residual = 100 − (% L + % T)

The concentrations of lidocaine in the oil phases of the melt systems analyzed were consistently higher than 80% (w:w) and reached as high as 87% (w:w) as evidenced by Melt System III. The sum of lidocaine and thymol in the oil phase was less than 100%, due to the presence of ethyl alcohol and possibly a trace amount of water. This also indicates that in the two-phase melt systems, nearly all of the ethyl alcohol is present in the aqueous phase. It can also be seen that the higher the initial L:T ratio, the higher the lidocaine concentration in the oil phase.

As shown in Table 5, the GC-MS data indicate that the concentrations of lidocaine and thymol in the aqueous phase of Melt System III were 1.09% and 0.09% (w:w), respectively. Based on the initial composition of the melt system and the concentrations of lidocaine and thymol in both the aqueous and oil phases, the quantities of lidocaine and thymol in both the aqueous phase and the oil phase were estimated. The results in Table 5 show that approximately 80% by weight of the total lidocaine and approximately 85% by weight of the total thymol are present in the oil phase, while the remaining amounts are present in the aqueous phase.

TABLE 5

Distribution of Lidocaine (L) and Thymol (T) Between Oil Phase and Aqueous Phase (aq) of Melt System III[a]

| | Conc in oil[b] % | Percentage in oil[c] % | Conc in aq[b] % | Percentage in aq[c] % |
|---|---|---|---|---|
| L | 87.00 | 79.20 | 1.09 | 20.80 |
| T | 10.60 | 85.13 | 0.09 | 14.88 |

[a]Source: Table 3
[b]Concentration in oil phase or aqueous phase = amount (g) detected per 100 g of oil phase or aqueous phase
[c]Percentage in oil phase or aqueous phase = amount (g) in oil phase or aqueous phase/total amount (g) in the whole system × 100

It can thus be seen that generation of a homogenous oil phase, as in the two phase melt systems shown in Table 3, depends on the relative amounts of the local anesthetic, LA, the first melting point depressing agent, MP-A, and the second melting point depressing agent, MP-B, in the systems. When thymol (as the MP-A) and/or ethyl alcohol (as the MP-B) are present in insufficient amounts, a two phase melt system is not achieved at ambient temperature, and instead crystals remain in the composition. A preferred two phase melt system is generally characterized by high lidocaine:thymol ratio and a relatively low amount of ethyl alcohol.

EXAMPLE 2

Melting Point Depression of Tetracaine by Thymol and Ethyl Alcohol

Replicate samples containing tetracaine, thymol, ethyl alcohol and water were prepared at 25° C. according to Table 6 and were stored at 25, 15 and 4° C. for three months. During storage, the melt states of the samples were examined weekly by an optical microscope.

TABLE 6

Generation of Two Phase Melt System Using Tetracaine

| | |
|---|---|
| Tetracaine | 4%[a] |
| Thymol | 0.44% |
| Ethyl alcohol | 0–20% |
| Water q.s. | 100% |

[a]% by weight

The results in Table 7 show that thymol and ethyl alcohol together can effectively depress the melting point of tetracaine as they depress the melting point of lidocaine.

TABLE 7

Melt States of Dispersions Containing Tetracaine (Tc), Thymol (T) Ethyl Alcohol (E) and Water at Different Temperatures

| Tc:T[a] | °C. | 0% E[a] | 10% E | 15% E | 20% E | 25% E |
|---|---|---|---|---|---|---|
| 90:10 | 25 | S | O | O | O | O |
| 90:10 | 15 | S | O | O | O | O |
| 90:10 | 4 | S | S | S | S | S |

[a]Tc:T and % E by weight
S - solid crystals present
O - oil without crystals

The two phase melt systems as in Table 7 containing tetracaine can be readily formulated into creams, emulsions or organogels for effective topical anesthesia on intact skin and mucous membrane.

EXAMPLE 3

Melting Point Depression of Lidocaine by Other Melting Point Depressing Agents

A. Substitutes for Thymol

When any or any combination of menthol, butylated hydroxytoluene, butylated hydroxyanisole, methyl salicylate, phenyl salicylate, S(+)-ibuprofen, R(-)-ibuprofen, ceneole, eugenol, tetracaine, prilocaine, benzocaine, etidocaine, bupivacaine and mepivacaine was used as a substitute (MP-A) for thymol and mixed with lidocaine, ethyl alcohol and water at the ratios shown in Table 8, two phase melt systems were spontaneously formed at 20–25° C.

TABLE 8

Compositions of Two-phase Melt Systems With Substitutes for Thymol

| | |
|---|---|
| Lidocaine | 5%[a] |
| MP-A | 0.88% |
| Ethyl alcohol | 15% |
| Water q.s. | 100% |

[a]% by weight

The two phase melt systems as in Table 8 can be readily formulated into creams, emulsions and organogels for effective topical anesthesia on intact skin.

B. Substitutes for Ethyl Alcohol

When any or any combination of isopropyl alcohol, propylene glycol, polyethylene glycol and ethyl alcohol was used as a substitute (MP-B) for ethyl alcohol, and was mixed with lidocaine, thymol and water at the ratios shown in Table 9, two phase melt systems were spontaneously formed at 20–25° C.

TABLE 9

Compositions of Two-phase Melt Systems With Substitutes for Ethyl Alcohol

| | |
|---|---|
| Lidocaine | 5%[a] |
| Thymol | 0.55% |
| MP-B | 10–40% |
| Water q.s. | 100% |

[a]% by weight

The two phase melt systems as in Table 9 can be readily formulated into creams, emulsions or organogels for effective topical anesthesia on intact skin.

EXAMPLE 4

Melting Point Depression of Other Local Anesthetic Agents (LA) by Thymol and Ethyl Alcohol When any of prilocaine, mepivacaine, procaine, benzocaine and bupivacaine was mixed with thymol, ethyl alcohol and water at the ratios shown in Table 10, two phase melt systems were spontaneously formed at 20–25° C.

TABLE 10

Compositions of Two-phase Melt Systems With Other Local Anesthetic Agents

| | |
|---|---|
| LA | 5%[a] |
| Thymol | 0.88% |
| Ethyl alcohol | 15% |
| Water q.s. | 100% |

[a]% by weight

The two phase melt systems as in Table 10 can be readily formulated into creams, emulsions or organogels for effective topical anesthesia on intact skin.

EXAMPLE 5

Preparation of a Lidocaine (L) Cream

To Melt System III in Table 3, 1% (w:w) of Carbopol NF980 (a thickening agent) and 1% of one or two surfactants (Tween and/or Span, Atlas Chemical Company) were added and emulsified after adjusting the pH of the formulation to 9.2. The overall concentration of lidocaine in the cream was 5% (w:w).

This represents a typical procedure to prepare a topical anesthetic cream from any of the two-phase melt systems described herein, and is not limited to the use of any particular surfactant and thickening agent. Advantageously, the two-phase melt systems can be directly formulated into a cream with the addition of selected thickening agent(s) and surfactant(s).

EXAMPLE 6

Preparation of a Tetracaine Cream

A topical cream was made using the components listed in Table 11. This represents a typical composition of a topical tetracaine cream based on the two phase melt systems.

TABLE 11

Composition of a Topical Tetracaine Cream
Using the Two-phase Melt System

| | |
|---|---|
| Tetracaine | 4%[a] |
| Thymol | 0.44% |
| Ethyl alcohol | 15% |
| Carbopol 980NF | 1% |
| Surfactant | 1% |
| Water q.s. | 100% |

[a]% by weight

A stable cream is obtained after emulsification which is highly effective to achieve transdermal anesthesia on intact skin.

EXAMPLE 7

In Vivo Efficacy Study of the 5% Lidocaine Cream in Mice

The in vivo efficacy of the 5% lidocaine cream (Example 5) was determined using the mice tail-flick model. This animal model has been widely used for the test of pain-control treatments (H. Aron et al., *J. Pharmacol. Exp. Ther.* 276:585–593 (1996); R. Zulma et al., *J. Pharmacol. Exp. Ther.* 278:304–312 (1996); L. Tseng et al., *J. Pharmacol. Exp. Ther.* 279:39–46 (1997)), since it was first reported in almost 60 years ago (F. D'Amour et al., *J. Pharmacol. Exp. Ther.* 72:74–78 (1941)). A mouse was put into a restrainer with the tail left outside. The focused light from an electric bulb (12V) was applied to the tip of the tail. The latency time for the mouse to react to the heat by flicking its tail was recorded with a millisecond stopwatch and used as the indication of the anesthetic activity of the medication.

In the present study, nine female mice weighing 25 g were randomly divided into three groups and tested in a blinded 3-way cross-over study. On three separate study days with one week wash-out period, 1 gram of the test and placebo formulations was filled into a 1 ml plastic centrifuge tube. The end of the mouse tail was carefully placed into the tube and secured with a tape. After application of the formulations for 80 minutes, the tail was removed from the tube and cleansed gently using wetted gauze. The pointed light source was then carefully applied to the tip of the tail from a set distance. The latency time (3–5 seconds) was measured with 3 replications within 3 minutes after the removal and cleansing of the formulation. The results shown in Table 12 were analyzed using an ANOVA test.

TABLE 12

Latency Time Reacting to Thermal Stimulus in Mice
After Receiving Different Treatments Latency Time in Seconds

| Mouse | Placebo | | | New Cream | | | EMLA | | |
|---|---|---|---|---|---|---|---|---|---|
| 1 | 3.17 | 3.87 | 3.69 | 4.89 | 4.40 | 5.17 | 4.41 | 4.61 | 4.55 |
| 2 | 3.42 | 3.84 | 3.17 | 3.96 | 4.73 | 3.56 | 3.49 | 4.69 | 4.23 |
| 3 | 2.33 | 2.50 | 2.27 | 3.67 | 3.30 | 3.79 | 3.70 | 4.16 | 4.53 |
| 4 | 2.05 | 2.86 | 2.79 | 4.19 | 4.43 | 5.48 | 3.44 | 4.31 | 4.33 |
| 5 | 3.93 | 3.13 | 3.25 | 5.86 | 4.93 | 6.00 | 4.99 | 4.17 | 4.65 |
| 6 | 2.89 | 3.50 | 3.30 | 4.36 | 4.29 | 4.76 | 6.00 | 6.00 | 5.41 |
| 7 | 2.81 | 3.13 | 3.43 | 3.69 | 2.54 | 3.10 | 2.53 | 3.17 | 3.03 |
| 8 | 2.43 | 3.02 | 2.63 | 4.10 | 4.09 | 3.66 | 4.03 | 3.92 | 4.98 |
| 9 | 3.10 | 2.20 | 2.38 | 3.71 | 3.30 | 4.23 | 3.97 | 3.44 | 2.99 |
| Mean | | 2.97 | | | 4.23 | | | 4.21 | |
| SD | | 0.52 | | | 0.82 | | | 0.85 | |

TABLE 13

ANOVA Restults For Data in Table 12

| Source | DF | MS | F | P > F |
|---|---|---|---|---|
| Model | | | | |
| Mouse | 8 | 2.5757 | 13.32 | 0.0001 |
| Formulation | 2 | 14.1646 | 73.25 | 0.0001 |
| Mouse × Formulation | 16 | 0.7741 | 4.00 | 0.0001 |
| Error | 54 | 0.1934 | | |
| Total | 80 | | | | t-tests:

New cream versus placebo: t=6.53, p=0.001

EMLA versus placebo: t=6.44, p=0.001

New cream versus EMLA: t=0.09, not significant

Based on the results shown in Table 12, it can be concluded that both the new cream (Example 5) and EMLA show a significant anesthetic effect on mice tail as compared with the placebo (p=0.001). No significant difference is found in the latency times between the new cream and EMLA (t=0.09).

EXAMPLE 8

In Vivo Efficacy Study of a 6% Lidocaine Cream and a 4% Tetracaine Cream in Human Subjects The anesthetic effects produced by a lidocaine cream, a tetracaine cream, EMLA cream and a placebo cream on intact skin of human volunteers (10 males and 4 females in 22–59 years old) were measured and compared in a randomized double-blind study. The compositions of the lidocaine (L) and tetracaine (Tc) creams tested are shown in Tables 14 and 15.

TABLE 14

Composition of 6%[a] Lidocaine Cream

| | |
|---|---|
| Lidocaine | 6 g |
| Thymol | 0.66 g |
| Isopropyl alcohol | 15 g |
| Carbopol 980NF | 1 g |
| Surfactant | 1 g |
| Water q.s. | 100 g |

[a]% by weight

TABLE 15

Composition of 4%[a] Tetracaine Cream

| | |
|---|---|
| Tetracaine | 4 g |
| Thymol | 0.44 g |

TABLE 15-continued

Composition of 4%[a] Tetracaine Cream

| Isopropyl alcohol | 15 g |
| Carbopol 980NF | 1 g |
| Surfactant | 1 g |
| Water q.s. | 100 g |

[a] % by weight

The EMLA (E) cream (Astra Pharmaceuticals, Inc.) was used as a reference product. The placebo cream was prepared by emulsifying 6 g of cotton seed oil instead of lidocaine according to Table 14.

Figure 2:
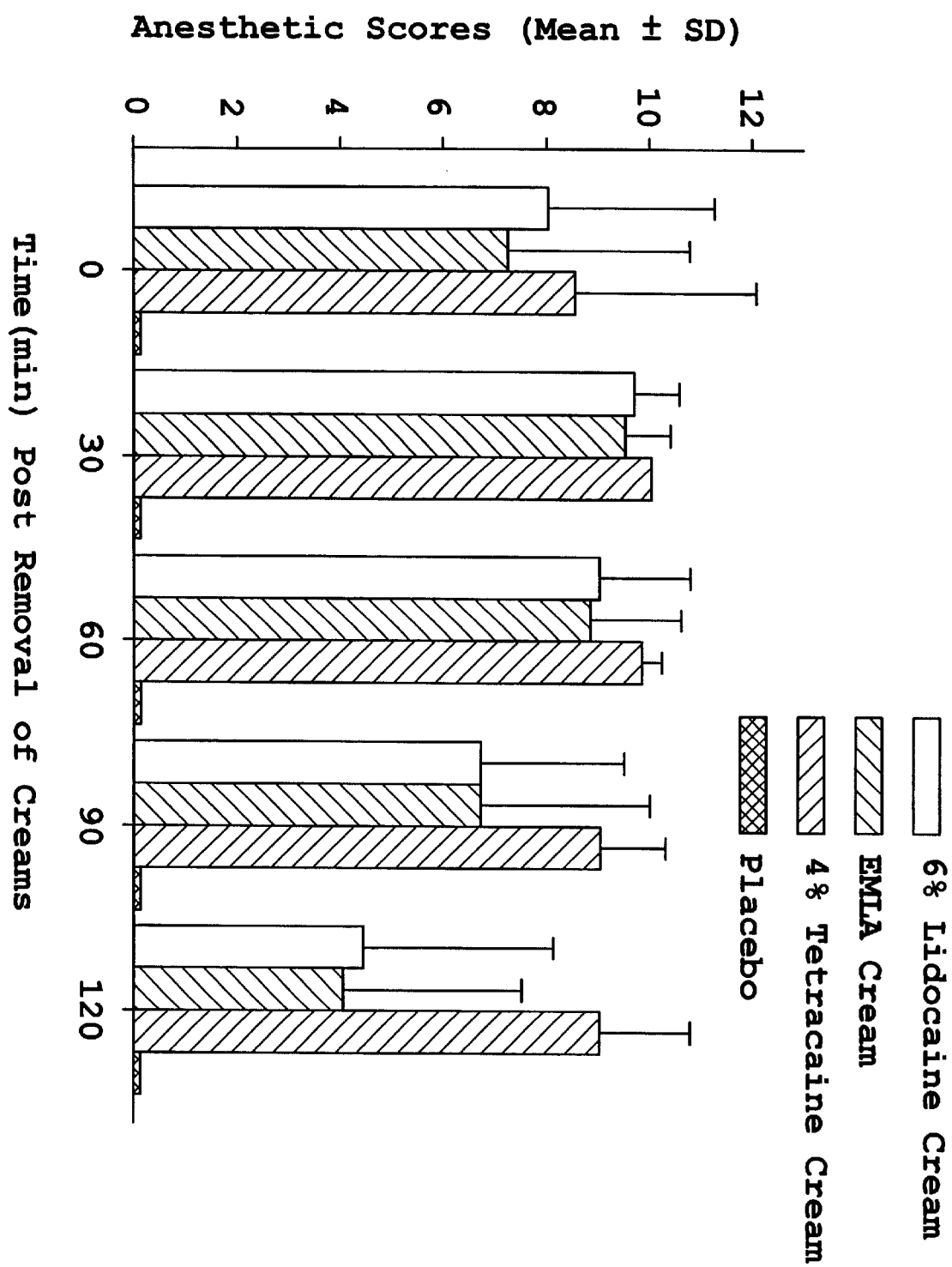
FIG. 2 shows anesthetic scores for various anesthetic cream formulations after 60 minute applications.

Informed consent was obtained from all the volunteers, and the study was approved by the Institutional Review Board of the University of Georgia. On the test date, each subject received the doses of 1 g of 6% L cream, 1 g of EMLA, 0.5 g of 4% Tc cream and 1 g of the placebo cream randomly applied on the volar surface of either right or left forearm. All applications were covered with Saran wrap. At the end of the 60 minute application time, the formulations were completely removed. Immediately after removal and at 30, 60, 90 120 minutes after removal, ten pin-pricks were applied using a sharp tooth-pick covering the entire drug application site. The subjects were required to record the number of times that he/she cannot feel pain. The number recorded was used as the anesthetic score for the efficacy test. The anesthetic scores at different testing times are plotted in FIG. 2. The duration of the anesthetic effects, defined as the length of the period during which the anesthetic scores remain higher than 5 after removal of the creams, are shown in Table 14.

The differences in the anesthetic scores and the duration of anesthesia among different creams were analyzed by ANOVA and Tukey's test.

Statistical Analysis for the Anesthetic Scores:

Immediately after removal of the creams ($t_p=0$ minutes):

The scores for Tc, L and EMLA creams were significantly higher than for placebo, and no significant differences were found among the scores for Tc, L and EMLA (p=0.05).

30 minutes post removal of the creams ($t_p=30$ minutes):

The scores for Tc, L and EMLA were significantly higher than for placebo; the scores for Tc is significantly higher than those for EMLA; no significant difference was found between Tc and L; no significant difference was found between L and EMLA (p=0.05).

60 minutes post removal of the creams ($t_p=60$ minutes):

The scores for Tc, L and EMLA were significantly higher than for placebo; no significant difference was found among Tc, L and EMLA (p=0.05).

90 minutes post removal of the creams ($t_p=90$ minutes):

The scores for Tc, L and EMLA were significantly higher than for placebo; the scores for Tc are significantly higher than for L and EMLA; no significant difference is found between L and EMLA (p=0.05).

120 minutes post removal of the creams ($t_p=120$ minutes):

The scores for Tc, L and EMLA were significantly higher than for placebo; the scores for Tc are significantly higher than for L and EMLA; no significant difference is found between L and EMLA (p=0.05).

Statistical Analysis for the Duration of Anesthesia:

The duration of anesthesia after application of 4% Tc cream following the application for 60 minutes is significantly longer than those of the 6% L and EMLA creams (p=0.01). There is no significant difference in the duration of anesthesia between the L cream and the EMLA cream following the same period of application (p=0.05).

TABLE 16

Duration[a] of Anesthesia After Application of Different Formulations for 60 minutes

| | Subject | | | | | | | | | | | | | | | |
| --- | --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 | Mean (SD) |
| L | 1.5 | 1.5 | 2.0 | 1.0 | 1.5 | 1.0 | 2.0 | 1.5 | 2.0 | 1.5 | 1.5 | 1.0 | 2.0 | 1.5 | 1.54 (0.36) |
| E | 1.5 | 1.0 | 1.5 | 1.0 | 1.5 | 1.0 | 2.0 | 1.0 | 2.0 | 1.5 | 1.5 | 1.0 | 2.0 | 2.0 | 1.46 (0.41) |
| Tc | 2.0 | 2.0 | 2.0 | 2.0 | 2.0 | 1.5 | 2.0 | 2.0 | 2.0 | 2.0 | 2.0 | 2.0 | 2.0 | 2.0 | 1.96 (0.13) |

[a] hours

Conclusions

The pin-prick tests showed that following the application time of 60 minutes, the 6% lidocaine cream and EMLA cream produced comparable anesthetic effects during the 2-hour period after removal of the creams. With respect to the anesthetic activity, the 4% tetracaine cream showed deeper transdermal anesthesia with longer duration than both the 6% lidocaine cream and EMLA cream. Due to safety considerations, the 6% lidocaine cream is preferred.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising one or more local anesthetic agents, wherein at least one local anesthetic agent is selected from the group consisting of lidocaine, procaine, mepivacaine, benzocaine, bupivacaine and etidocaine; said composition having an aqueous phase and an oil phase at 25°, wherein the concentration of one selected local anesthetic agent in the oil phase is, by weight, at least about 70% of the weight of the oil phase.

2. The composition of claim 1 wherein the concentration of the one selected local anesthetic agent in the oil phase is, by weight, at least about 85% of the weight of the oil phase.

3. The composition of claim 1 wherein the oil phase is homogenous at about 37° C.

4. The composition of claim 1 wherein the oil phase is homogenous at about 25° C.

5. The composition of claim 1 wherein the aqueous phase is homogenous at about 37° C.

6. The composition of claim 1 wherein the aqueous phase is homogenous at about 25° C.

7. The composition of claim 1 wherein the one selected local anesthetic agent is lidocaine.

8. The composition of claim 1 further comprising a first melting point depressing agent.

9. The composition of claim 8 wherein the first melting point depressing agent is selected from the group consisting of thymol, menthol, methyl salicylate, phenyl salicylate, butylated hydroxytoluene, butylated hydroxyanisole, S(+)-ibuprofen, R(−)-ibuprofen, cineole, eugenol, capsaicin, eucalyptol, a local anesthetic agent and any combination thereof.

10. The composition of claim 9 wherein the first melting point depressing agent comprises thymol.

11. The composition of claim 9 wherein the first melting point depressing agent comprises menthol.

12. The composition of claim 9 wherein the first melting point depressing agent comprises S-(+)-ibuprofen.

13. The composition of claim 8 further comprising a second melting point depressing agent.

14. The composition of claim 13 wherein the second melting point depressing agent is an alcohol.

15. The composition of claim 14 wherein the alcohol is selected from the group consisting of isopropyl alcohol, ethyl alcohol, propylene glycol, polyethylene glycol and any combination thereof.

16. The composition of claim 14 wherein the alcohol comprises isopropyl alcohol.

17. The composition of claim 14 wherein the alcohol comprises ethyl alcohol.

18. The composition of claim 13 wherein the one selected local anesthetic agent is about 1% to about 20% of the total composition, by weight; the first melting point depressing agent is present in the composition in an amount of about 1/20 to about 2/3 of the weight of the local anesthetic agent; and the second melting point depressing agent is about 1% to about 30% of the total composition, by weight.

19. The composition of claim 18 wherein the one selected local anesthetic agent is lidocaine, the first melting point depressing agent comprises at least one of thymol and menthol, and the second melting point depressing agent comprises at least one of ethyl alcohol and isopropyl alcohol.

20. A topical anesthetic preparation comprising at least a therapeutically effective amount of a portion of the oil phase of the composition of claims 1 or 18 and at least one selected from the group consisting of a pharmaceutically acceptable excipient and a pharmaceutically acceptable miscible solvent.

21. The preparation of claim 20 further comprising at least a portion of the aqueous phase of the composition of claim 1.

22. The preparation of claim 20 further comprising at least a portion of the aqueous phase of the composition of claim 21.

23. The topical anesthetic preparation of claim 20 formulated as a cream, emulsion, ointment, lotion, organogel, transdermal patch, plaster, or occlusive dressing.

24. The preparation of claim 23 which is a cream.

25. The preparation of claim 23 which is a transdermal patch.

26. A topical anesthetic preparation comprising the composition of claim 1 with at least one pharmaceutically acceptable excipient.

27. A method for making a topical anesthetic preparation comprising mixing the composition of claim 1 with at least one pharmaceutically acceptable excipient.

28. The method of claim 27 wherein the preparation is formulated as a cream, emulsion, ointment, lotion, organogel, transdermal patch, plaster, or occlusive dressing.

29. A preparation for use in transdermal anesthesia comprising:
a homogenous oil comprising one or more local anesthetic agents, wherein at least one local anesthetic agent is selected from the group consisting of lidocaine, procaine, mepivacaine, benzocaine, bupivacaine and etidocaine; and wherein the concentration of one selected local anesthetic agent is, by weight, of at least about 70% of the weight of the oil; and
a pharmaceutically acceptable miscible solvent.

30. A composition comprising a single local anesthetic agent; a first melting point depressing agent selected from the group consisting of thymol, menthol, methyl salicylate, phenyl salicylate, butylated hydroxytoluene, butylated hydroxyanisole, S(+)-ibuprofen, R(−)-ibuprofen, cineole, eugenol, capsaicin, eucalyptol, and any combination thereof; a second melting point depressing agent comprising an alcohol; and water; said composition having an aqueous phase and an oil phase at 25° C., wherein the concentration of the local anesthetic agent in the oil phase is, by weight, at least about 60% of the weight of the oil phase.

31. The composition of claim 30 wherein the concentration of the local anesthetic agent in the oil phase is, by weight, at least about 70% of the weight of the oil phase.

32. The composition of claim 30 wherein the concentration of the local anesthetic agent in the oil phase is, by weight, at least about 85% of the weight of the oil phase.

33. The composition of claim 30 wherein the local anesthetic agent is selected from the group consisting of lidocaine, tetracaine, prilocaine, procaine, mepivacaine, benzocaine, bupivacaine and etidocaine.

34. The composition of claim 30 wherein the local anesthetic agent is lidocaine.

35. The composition of claim 30 wherein the local anesthetic agent is tetracaine.

36. The composition or of claim 30 wherein the first melting point depressing agent comprises thymol.

37. The composition of claim 30 wherein the first melting point depressing agent comprises menthol.

38. The composition of claim 30 wherein the first melting point depressing agent comprises S-(+)-ibuprofen.

39. The composition of claim 30 wherein the alcohol is selected from the group consisting of isopropyl alcohol, ethyl alcohol, propylene glycol, polyethylene glycol and any combination thereof.

40. The composition of claim 39 wherein the alcohol comprises isopropyl alcohol.

41. The composition of claim 39 wherein the alcohol comprises ethyl alcohol.

42. The composition of claim 30 wherein the local anesthetic agent is about 1% to about 20% of the total composition, by weight; the first melting point depressing agent is present in the composition in an amount of about 1/20 to about 2/3 of the weight of the local anesthetic agent; and the second melting point depressing agent is about 1% to about 30% of the total composition, by weight.

43. The composition of claim 30 wherein the local anesthetic agent is lidocaine or tetracaine, the first melting point depressing agent comprises an agent selected from the group consisting of thymol and menthol, and the second melting point depressing agent comprises an alcohol selected from the group consisting of ethyl alcohol and isopropyl alcohol.

44. The composition of claim 43 wherein the local anesthetic agent is lidocaine.

45. A topical anesthetic preparation comprising at least a portion of the oil phase of the composition of claim 30 and at least one component selected from the group consisting of a pharmaceutically acceptable excipient and a pharmaceutically acceptable miscible solvent.

46. The topical anesthetic preparation of claim 45 wherein the local anesthetic agent is lidocaine or tetracaine, the first melting point depressing agent comprises an agent selected from the group consisting of thymol and menthol, and the second melting point depressing agent comprises at least one alcohol selected from the group consisting of ethyl alcohol and isopropyl alcohol.

47. The topical anesthetic preparation of claim 45 formulated as a cream, emulsion, ointment, lotion, organogel, transdermal patch, plaster, or occlusive dressing.

48. A composition comprising lidocaine, thymol, at least one alcohol, and water; the composition having an aqueous phase and an oil phase at 25° C., wherein the concentration of lidocaine in the oil phase is, by weight, at least about 80% of the weight of the oil phase.

49. A homogenous oil comprising at least about 80% lidocaine, by weight, and thymol.

50. A topical anesthetic preparation comprising:
    a homogeneous oil comprising about 80% lidocaine, by weight, and thymol; and
    at least one component selected from the group consisting of a pharmaceutically acceptable excipient and a pharmaceutically acceptable miscible solvent.

51. The topical anesthetic preparation of claim 50 formulated as a cream, emulsion, ointment, lotion, organogel, transdermal patch, plaster, or occlusive dressing.

52. A method for making a two phase liquid composition comprising:
    mixing one or more local anesthetic agents, wherein at least one local anesthetic agent is selected from the group consisting of lidocaine, procaine, mepivacaine, benzocaine, bupivacaine and etidocaine; a first melting point depressing agent; a second melting point depressing agent; and water;
    to form a composition having an aqueous phase and an oil phase at 25° C., said oil phase comprising at least a portion of the local anesthetic agent, wherein the concentration of one selected local anesthetic agent in the oil phase is, by weight, at least about 70% of the weight of the oil phase.

53. The method of claim 52 wherein the one selected local anesthetic agent is a solid prior to mixing.

54. The method of claim 52 wherein the first melting point depressing agent is a solid prior to mixing.

55. The method of claim 52 wherein the composition has a homogenous aqueous phase and a homogenous oil phase at about 37° C.

56. The method of claim 52 wherein the composition has a homogenous aqueous phase and a homogenous oil phase at about 25° C.

57. The method of claim 52 wherein the one selected local anesthetic agent is lidocaine.

58. The method of claim 52 wherein the first melting point depressing agent is selected from the group consisting of thymol, menthol, methyl salicylate, phenyl salicylate, butylated hydroxytoluene, butylated hydroxyanisole, S(+)-ibuprofen, R(-)-ibuprofen, cineole, eugenol, capsaicin, eucalyptol, a local anesthetic agent and any combination thereof.

59. The method of claim 52 wherein the second melting point depressing agent is an alcohol selected from the group consisting of isopropyl alcohol, ethyl alcohol, propylene glycol, polyethylene glycol and any combination thereof.

60. A method for making an oil comprising a therapeutic agent, said method comprising mixing a therapeutic agent, a first melting point depressing agent selected from the group consisting of thymol, menthol, methyl salicylate, phenyl salicylate, butylated hydroxytoluene, butylated hydroxyanisole, S(+)-ibuprofen, R(-)-ibuprofen, cineole, eugenol, capsaicin, eucalyptol, a local anesthetic agent and any combination thereof, a second melting point depressing agent comprising an alcohol, and water to form a composition having an aqueous phase and an oil phase at 25° C. wherein the concentration of the therapeutic agent in the oil phase is, by weight, at least about 70% of the weight of the oil phase.

61. The method of claim 60 wherein the alcohol is ethyl alcohol.

62. The method of claim 60 wherein the alcohol is isopropyl alcohol.

63. The method of claim 60 wherein the at least one melting point depressing agent comprises a plurality of melting point depressing agents.

64. The method of claim 60 wherein the first melting point depressing agent comprises a local anesthetic agent selected from the group consisting of lidocaine, tetracaine, prilocaine, procaine, mepivacaine, benzocaine, bupivacaine, and etidocaine.

65. A method for obtaining transdernal anesthesia, said method comprising applying the topical anesthetic preparation of claim 20 to the intact skin or mucous membrane of an animal.

66. The method of claim 65 wherein the topical anesthetic preparation is applied to the intact skin of an animal.

67. The method of claim 65 wherein the animal is a human.

68. The method of claim 65 further comprising, after the applying step, covering the topical anesthetic preparation with a dressing.

69. The method of claim 65 performed prior to surgical incision, dental work, vaccination or needle insertion.

* * * * *